(12) United States Patent
Yasui et al.

(10) Patent No.: US 10,302,668 B2
(45) Date of Patent: May 28, 2019

(54) AUTOMATED ANALYZER DEVICE

(71) Applicant: HITACHI HIGH-TECHNOLOGIES CORPORATION, Tokyo (JP)

(72) Inventors: Akihiro Yasui, Tokyo (JP); Yoshihiro Suzuki, Tokyo (JP); Kazuhiro Nakamura, Tokyo (JP); Hitoshi Tokieda, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 190 days.

(21) Appl. No.: 15/109,475

(22) PCT Filed: Jan. 5, 2015

(86) PCT No.: PCT/JP2015/050070
§ 371 (c)(1),
(2) Date: Jul. 1, 2016

(87) PCT Pub. No.: WO2015/105079
PCT Pub. Date: Jul. 16, 2015

(65) Prior Publication Data
US 2016/0327587 A1  Nov. 10, 2016

(30) Foreign Application Priority Data
Jan. 7, 2014  (JP) .................................. 2014-001070

(51) Int. Cl.
G01N 35/10 (2006.01)
G01N 35/04 (2006.01)

(52) U.S. Cl.
CPC ..... *G01N 35/1011* (2013.01); *G01N 35/1079* (2013.01); *G01N 2035/0412* (2013.01);
(Continued)

(58) Field of Classification Search
CPC .......... G01N 35/1011; G01N 35/1079; G01N 2035/0412; G01N 2035/0453; G01N 2035/1025
(Continued)

(56) References Cited

U.S. PATENT DOCUMENTS 5,439,646 A   8/1995  Tanimizu et al.
6,171,280 B1  1/2001  Imazu et al.
(Continued)

FOREIGN PATENT DOCUMENTS

EP   0 984 285 A2   3/2000
EP   2 420 848 A2   2/2012
(Continued)

OTHER PUBLICATIONS

International Search Report of PCT/JP2015/050070 dated Mar. 3, 2015.
(Continued)

*Primary Examiner* — Robert R Raevis
(74) *Attorney, Agent, or Firm* — Mattingly & Malur, PC

(57) ABSTRACT

In a case where a sample container 15 has a rubber-made lid 35, if a sample nozzle descends and comes into contact with the lid, the sample nozzle is relatively moved inside an arm as far as a lid detection distance, and a detector detects a detection plate. A fact that the sample nozzle comes into contact with the lid is stored together with position information of the sample nozzle, into an operation commanding unit. The sample nozzle further continues to descend, and a suction operation of a sample is performed at a predetermined position. In a case where the sample nozzle collides with a frame portion of the lid and external force is applied thereto, the detector detects that the detection plate is relatively moved as far as the detection distance.

9 Claims, 13 Drawing Sheets

(52) U.S. Cl.
CPC ............. *G01N 2035/0453* (2013.01); *G01N 2035/1025* (2013.01)

(58) Field of Classification Search
USPC ........... 73/53.01, 61.41, 61.43, 61.48, 64.56, 73/863.01, 864.21, 864.24, 864.25, 73/864.81; 422/63, 67, 68.1, 422/82.05–82.11; 435/13, 69.6, 70.4; 356/39–41
See application file for complete search history.

(56) References Cited

U.S. PATENT DOCUMENTS

| | | | |
|---|---|---|---|
| 6,270,726 | B1 | 8/2001 | Tyberg et al. |
| 6,363,802 | B1 | 4/2002 | Grippo et al. |
| 2014/0273268 | A1* | 9/2014 | Cerra ............ G01N 35/10 436/180 |

FOREIGN PATENT DOCUMENTS

| | | |
|---|---|---|
| JP | 61-275660 A | 12/1986 |
| JP | 63-58166 A | 3/1988 |
| JP | 2000-088862 A | 3/2000 |
| JP | 2008-046002 A | 2/2008 |
| JP | 2013-019823 A | 1/2013 |
| JP | 2013-525817 A | 6/2013 |
| WO | 2013/042404 A1 | 3/2013 |

OTHER PUBLICATIONS

International Preliminary Report on Patentability received in corresponding International Application No. PCT/JP2015/050070 dated Jul. 21, 2016.
Chinese Office Action received in corresponding Chinese Application No. 201580003170.8 dated Nov. 30, 2016.
Chinese Office Action received in corresponding Chinese Application No. 201580003170.8 dated Aug. 9, 2017.
Extended European Search Report received in corresponding European Application No. 15734929.1 dated Oct. 18, 2017.
Chinese Office Action received in corresponding Chinese Application No. 201580003170.8 dated Mar. 27, 2018.

* cited by examiner

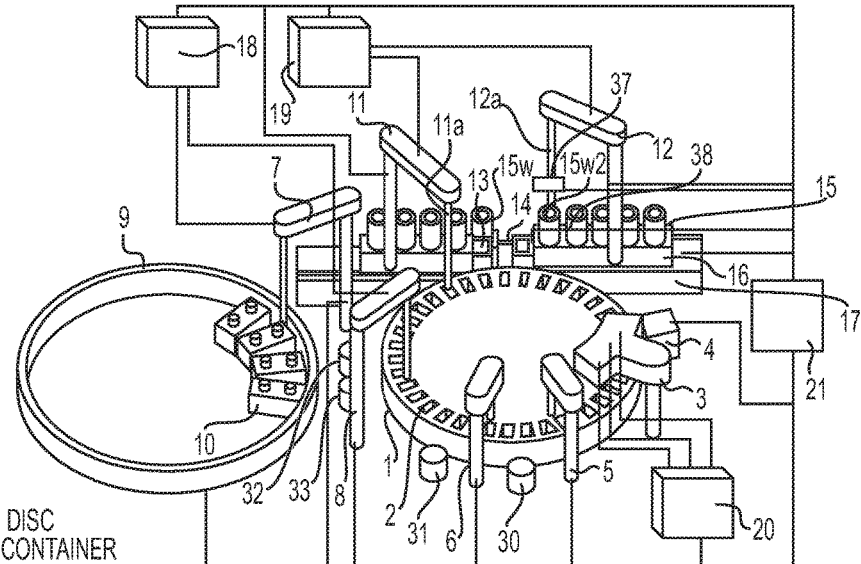

1. REACTION DISC
2. REACTION CONTAINER
3. WASHING MECHANISM
4. SPECTROPHOTOMETER
5. MIXING MECHANISM
6. MIXING MECHANISM
7. REAGENT DISPENSING MECHANISM
8. REAGENT DISPENSING MECHANISM
9. REAGENT DISC
10. REAGENT BOTTLE
11. SAMPLE DISPENSING MECHANISM
11a. SAMPLE NOZZLE
12. SAMPLE DISPENSING MECHANISM
12a. SAMPLE NOZZLE
13. WASHING TANK
14. WASHING TANK
15. SAMPLE CONTAINER
15w. SAMPLE SUCTION POSITION
15w2. SAMPLE SUCTION POSITION
16. RACK
17. SAMPLE CONVEYANCE MECHANISM
18. REAGENT PUMP
19. SAMPLE PUMP
20. WASHING PUMP
21. CONTROLLER
30. WASHING TANK
31. WASHING TANK
32. WASHING TANK
33. WASHING TANK
37. SAMPLE CONTAINER FIXING MECHANISM
38. RACK FIXING MECHANISM

FIG. 1

[Fig. 2]
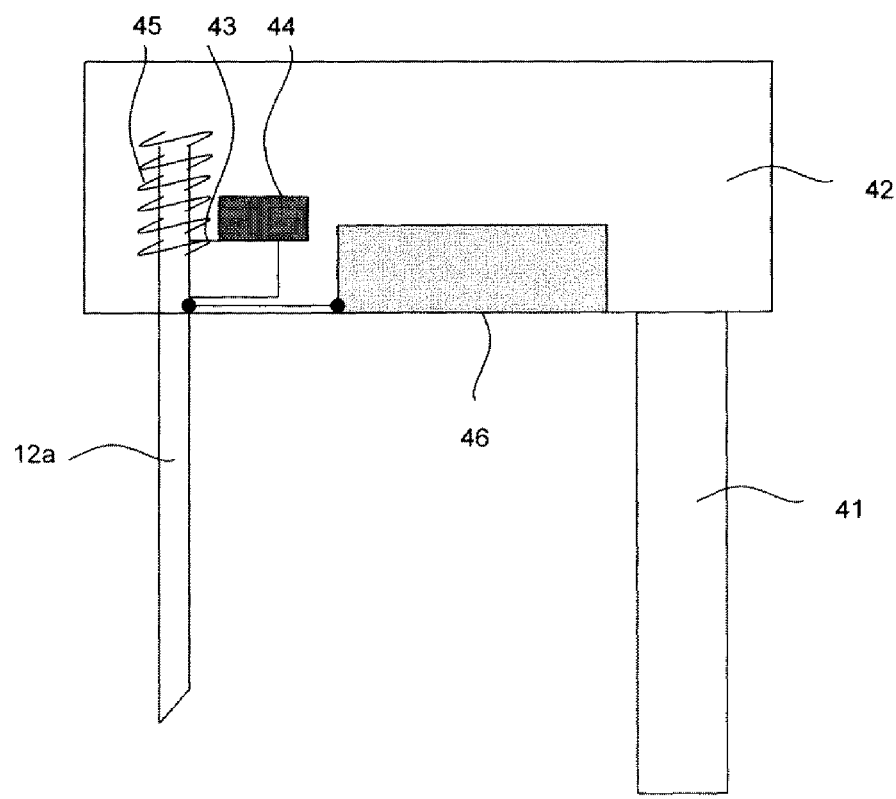
12a. SAMPLE NOZZLE
41. VERTICALLY ROTATING MECHANISM
42. ARM
43. DETECTION PLATE
44. DETECTOR
45. ELASTIC BODY
46. CAPACITANCE DETECTOR

- 12a. SAMPLE NOZZLE
- 15. SAMPLE CONTAINER
- 16. RACK
- 35. LID (RUBBER PORTION)
- 36. LID (FRAME)
- 37. SAMPLE CONTAINER FIXING MECHANISM
- 38. RACK FIXING MECHANISM

[Fig. 11]
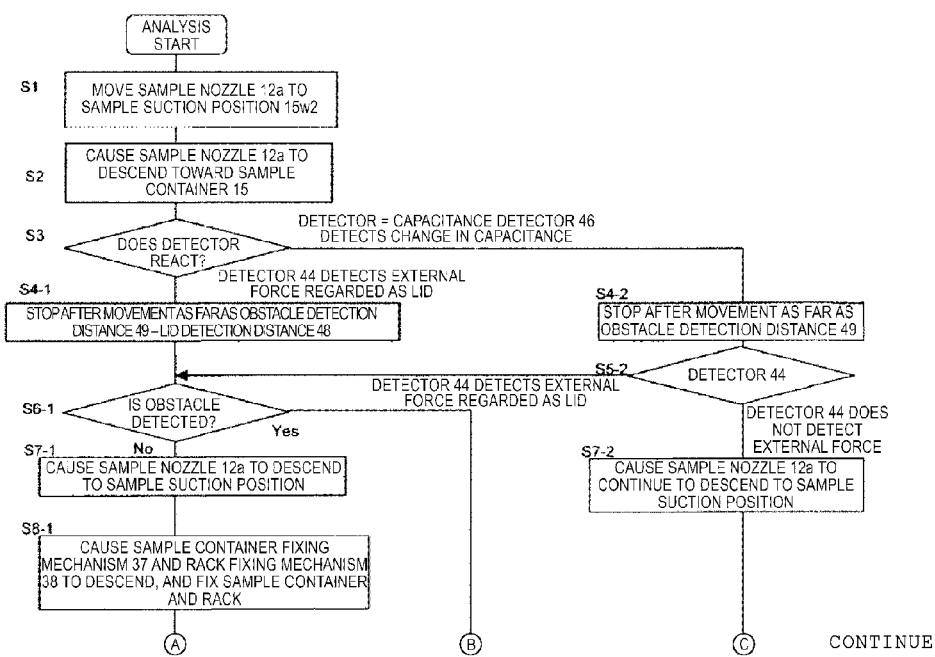

[Fig. 11] (continued)
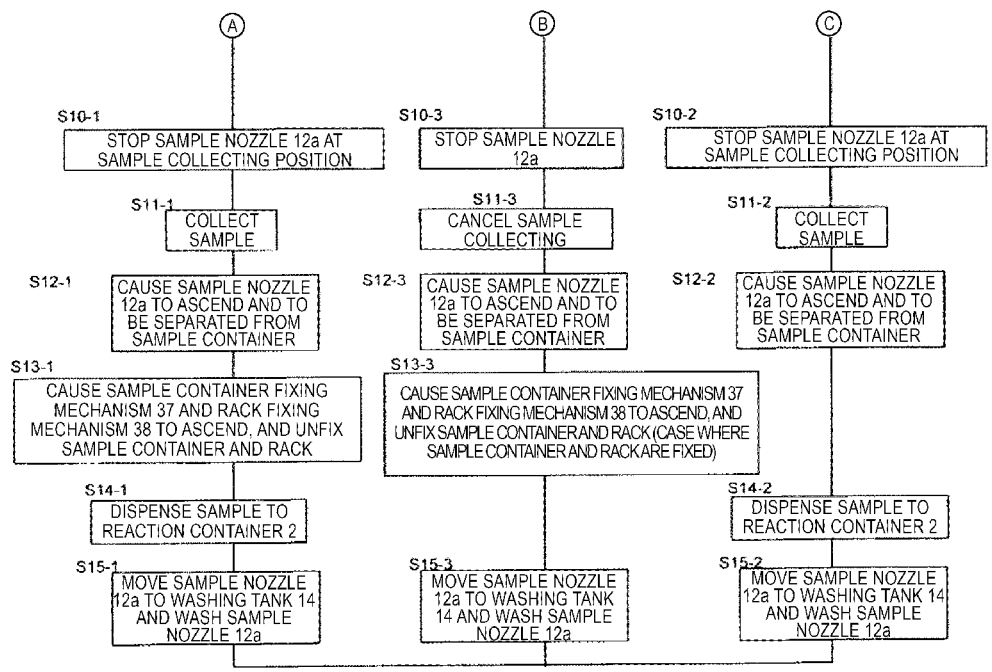

AUTOMATED ANALYZER DEVICE

TECHNICAL FIELD

The present invention relates to an automatic analysis device including a sample dispensing device.

BACKGROUND ART

An automatic analysis device for performing quantitative analysis or qualitative analysis on a specific component contained in a biological sample such as blood and urine is indispensable for currently performed diagnosis in view of reproducing an analysis result and improving processing speed.

In a case of sample containers used for the automatic analysis device, there are a sample container which is closed by a stopper and a sample container which is not closed by the stopper.

The sample container having the stopper and the sample container having no stopper are mixed with each other for use in the automatic analysis device. Therefore, according to a technique disclosed in PTL 1, a liquid suction device includes an external force detection sensor which detects that an upward external force is applied to a sample nozzle. The liquid suction device has the following configuration. When the sample nozzle is moved toward the sample container, in a case where the sample nozzle does not collide with the stopper and the external force is not applied, it is determined as the sample container which is not closed by the stopper. In a case where the sample nozzle collides with the stopper and the external force is applied, it is determined as the container which is closed by the stopper. Then, depending on whether or not the stopper is present, the sample nozzle is operated in accordance with specifications suitable for each container.

In addition, according to a technique disclosed in PTL 2, a diagnosis system is configured to determine that the upward external force is applied to the sample nozzle, by monitoring resistance inside a motor, and to detect whether or not the sample container has the stopper, or to detect whether or not the sample nozzle comes into contact with a bottom portion of the sample container.

CITATION LIST

Patent Literature

PTL 1: JP-A-2000-88862
PTL 2: JP-T-2013-525817

SUMMARY OF INVENTION

Technical Problem

According to the above-described techniques disclosed in PTL 1 and PTL 2, whether or not the stopper (lid) of the sample container is present is determined by external force detecting means including a sensor which detects that an object collides with a tip of the sample nozzle. Therefore, it is possible to determine whether or not the external force is applied after the sample nozzle collides with something. However, for example, the techniques do not reach a level for determining whether the object is rubber of the lid, a lid frame in an edge of the rubber, or other obstacles.

Despite the fact that the external force is detected at a portion other than the rubber of the lid, if the nozzle is operated after it is erroneously determined as the sample container having the lid, an excessive load is applied to the nozzle and a drive mechanism, thereby causing a possibility of damage. The reason is that in a case where the lid of the sample container is made of rubber, the sample nozzle is operated so that the sample nozzle pierces the rubber-made lid, and is inserted into the sample container to perform suction on a sample.

Based on a position where the sample nozzle detects the external force, whether or not it is the container having the lid can be determined. However, dimension information such as a height of the sample container needs to be registered into a device in advance. Depending on a manufacturer, a type or a shape of the sample container varies. Thus, it is difficult to cope with all types of the sample container. Therefore, if the determination is made based on the position where the external force is detected, there is a possibility that whether or not it is the container having the lid may be erroneously determined.

The problem in the above-described sample dispensing mechanism may also similarly occur even in a case where a reagent is dispensed from a reagent container in a reagent dispensing mechanism.

An object of the present invention is to realize an automatic analysis device which can properly control an operation of a dispensing nozzle by identifying a target with which the dispensing nozzle comes into contact, and which can avoid damage to the dispensing nozzle.

Solution to Problem

In order to achieve the above-described object, the present invention is configured as follows.

An automatic analysis device according to the present invention includes a nozzle that performs suction on a reagent or a sample, and that discharges the reagent or the sample to a reaction container, a dispensing mechanism that has an arm unit for supporting the nozzle, and that moves the arm unit in vertical and horizontal directions, an elastic support member that is arranged in the arm unit, and that supports the nozzle so as to be movable relative to the arm unit in the vertical direction, a relative movement distance detector that is arranged in the arm unit, and that detects a relative movement distance of the nozzle with respect to the arm unit, a suction/discharge mechanism that causes the nozzle to perform suction on the reagent or the sample, and that causes the nozzle to discharge the reagent or the sample to the reaction container, a photometer that emits light to the sample inside the reaction container so as to detect light intensity, and a controller that controls each operation of the dispensing mechanism, the suction/discharge mechanism, and the photometer, and that analyzes the sample inside the reaction container, based on the light intensity detected by the photometer.

Then, in accordance with the relative movement distance of the nozzle with respect to the arm unit which is detected by the relative movement distance detector, the controller determines whether a target with which a tip portion of the nozzle comes into contact is a lid portion into which the nozzle can be inserted or a member into which the nozzle cannot be inserted, in the sample container or the reagent container. Based on the determination, the controller controls the operation of the dispensing mechanism and the suction/discharge mechanism.

Advantageous Effects of Invention

According to the present invention, it is possible to realize an automatic analysis device which can properly control an operation of a dispensing nozzle by identifying a target with which the dispensing nozzle comes into contact, and which can avoid damage to the dispensing nozzle.

BRIEF DESCRIPTION OF DRAWINGS

FIG. 1 is a schematic configuration diagram of an automatic analysis device to which the present invention is applied.

FIG. 2 is a schematic configuration diagram of a sample dispensing mechanism according to Embodiment 1 of the present invention.

FIG. 11 is an operation flowchart according to Embodiment 3.

DESCRIPTION OF EMBODIMENTS

Figure 3:
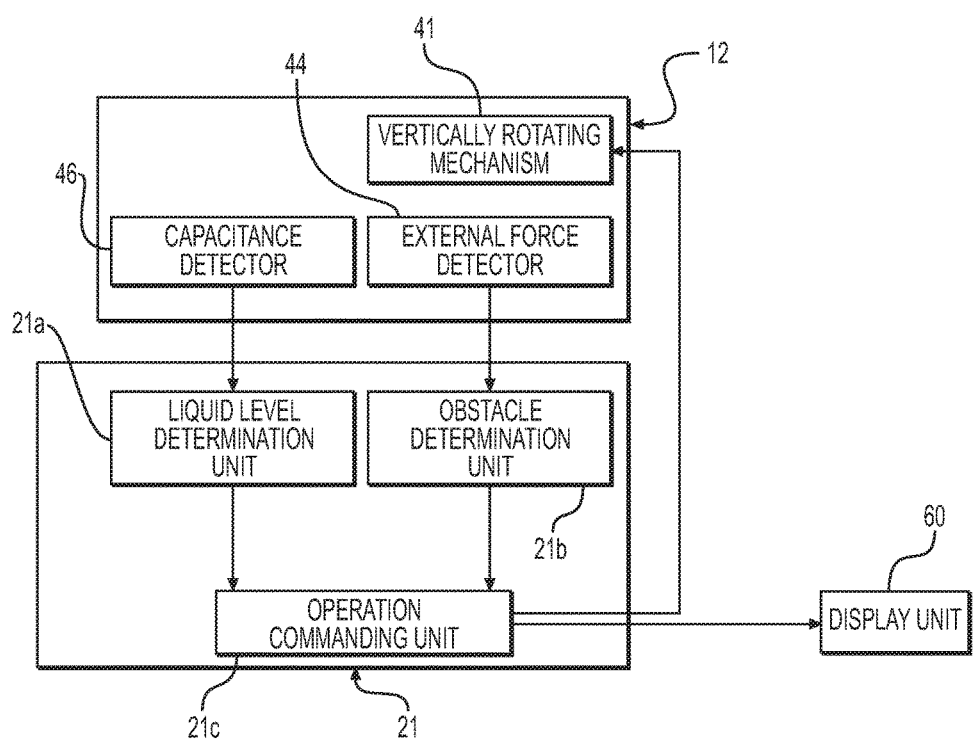
FIG. 3 is a functional block diagram relating to an operation control of the sample dispensing mechanism according to Embodiment 1 of the present invention.

Hereinafter, embodiments according to the present invention will be described with reference to the drawings.

Embodiments (Embodiment 1)

FIG. 1 is a schematic configuration diagram of an automatic analysis device to which Embodiment 1 according to the present invention is applied.

In FIG. 1, a plurality of reaction containers 2 are circumferentially juxtaposed in a reaction disc 1. In addition, a plurality of reagent bottles 10 can be circularly arranged in a reagent disc 9. A sample conveyance mechanism 17 which moves a rack 16 having a sample container 15 mounted thereon is installed in the vicinity of the reaction disc 1. Then, reagent dispensing mechanisms 7 and 8 which perform suction of a reagent from the reagent bottles 10 and discharge the reagent into a reaction container 2 are installed between the reaction disc 1 and the reagent disc 9.

In addition, a sample dispensing mechanism 11 which is rotatable and vertically movable and which can collect a sample from only a stopper-opened container, and a sample dispensing mechanism 12 which can collect the sample from both the stopper-opened container and a stopper-closed container are installed between the reaction disc 1 and the sample conveyance mechanism 17.

The sample dispensing mechanism 11 includes a sample dispensing nozzle (also referred to as a sample nozzle) 11a. A sample pump 19 is connected to the sample nozzle 11a. The sample nozzle 11a moves while drawing an arc around a rotation axis of the sample dispensing mechanism 11 so as to dispense the sample by performing suction of the sample from the sample container 15 and discharging the sample to the reaction container 2.

The sample dispensing mechanism 12 includes a sample dispensing nozzle 12a. The sample pump 19 is connected to the sample nozzle 12a. The sample nozzle 12a moves while drawing an arc around a rotation axis of the sample dispensing mechanism 12 so as to dispense the sample by performing suction of the sample from the sample container 15 and discharging the sample to the reaction container 2.

The reaction container 2, a washing mechanism 3, a spectrophotometer 4, mixing mechanisms 5 and 6, the reagent disc 9, and the sample conveyance mechanism 17 are arranged around the reaction disc 1, and a washing pump 20 is connected to the washing mechanism 3. Washing tanks 13, 14, 30, 31, 32, and 33 are respectively installed on an operation range of the reagent dispensing mechanisms 7 and 8, the sample dispensing mechanism 11, and the mixing mechanisms 5 and 6. A reagent pump 18 is connected to the reagent dispensing mechanisms 7 and 8.

The sample container 15 contains a test sample such as blood, and is conveyed by the sample conveyance mechanism 17 after being mounted on the rack 16. The sample dispensing mechanism 11 performs suction of the sample from the sample container 15 located at a sample suction position 15w. The sample dispensing mechanism 12 performs suction of the sample from the sample container 15 located at a sample suction position 15w2.

A sample container fixing mechanism 37 is arranged above the sample suction position 15w2. In a case where the sample container 15 located at the sample suction position 15w2 has a lid, the sample container fixing mechanism 37 holds the sample container so that the sample container does not rise and deviate from the rack after the sample dispensing mechanism 12 performs suction of the sample. The sample container fixing mechanism 37 is not necessarily needed in Embodiment 1, and is needed in Embodiment 2 (to be described later).

A rack fixing mechanism 38 is arranged above the rack 16. In a case where the sample container 15 located at the sample suction position 15w2 has the lid, the rack fixing mechanism 38 presses the rack against the sample conveyance mechanism so that the rack 16 does not rise together with the sample container after the sample dispensing mechanism 12 performs suction of the sample. The rack fixing mechanism 38 is not necessarily needed in Embodiment 1, and is needed in Embodiment 2 (to be described later).

In addition, the above-described respective mechanisms are connected to a controller 21, and each operation thereof is controlled by the controller 21. In addition, the controller 21 has a function as an analysis unit that analyzes a test sample inside the reaction container 2.

FIG. 2 is a schematic configuration diagram of the sample dispensing mechanism 12 according to Embodiment 1 of the present invention. In FIG. 2, the sample dispensing mechanism 12 is configured to include a sample nozzle 12a which performs suction and discharging of the sample, an arm 42 which holds the sample nozzle 12a, an elastic body (spring) 45 which elastically supports the sample nozzle 12a, a capacitance detector (liquid level detector) 46 which detects a capacitance change in the sample nozzle 12a, an obstacle detection plate 43 which is fixed to the sample nozzle 12a, an obstacle detector (external force detector) 44 which detects the movement of the obstacle detection plate 43, and a vertically rotating mechanism 41 which vertically and rotatably operating the arm 42. The obstacle detection plate 43 and the obstacle detector 44 form a relative movement distance detector which detects a relative movement distance of the sample nozzle 12a with respect to the arm 42.

FIG. 3 is a functional block diagram of the controller 21, which relates to an operation control of the sample dispensing mechanism 12 according to Embodiment 1 of the present invention. In FIG. 3, the controller 21 includes an obstacle determination unit 21a, a liquid level determination unit 21b, and an operation commanding unit 21c.

A capacitance detection signal of the capacitance detector 46 of the sample dispensing mechanism 12 is supplied to the liquid level determination unit 21b. A liquid level determination signal is supplied from the liquid level determination unit 21b to the operation commanding unit 21c. In addition, an output signal is supplied from the obstacle detector 44 of the sample dispensing mechanism 12 to the obstacle determination unit 21a. An obstacle determination signal is supplied from the obstacle determination unit 21b to the operation commanding unit 21c. Based on the liquid level determination signal supplied from the liquid level determination unit 21a and the obstacle determination signal supplied from the obstacle determination unit 21a, the operation commanding unit 21c supplies an operation command signal to the vertically rotating mechanism of the sample dispensing mechanism 42.

Although not illustrated in FIG. 1, the automatic analysis device to which the present invention is applied includes a display unit 60. The operation commanding unit 21c supplies a display command to the display unit 60.

Figure 4:
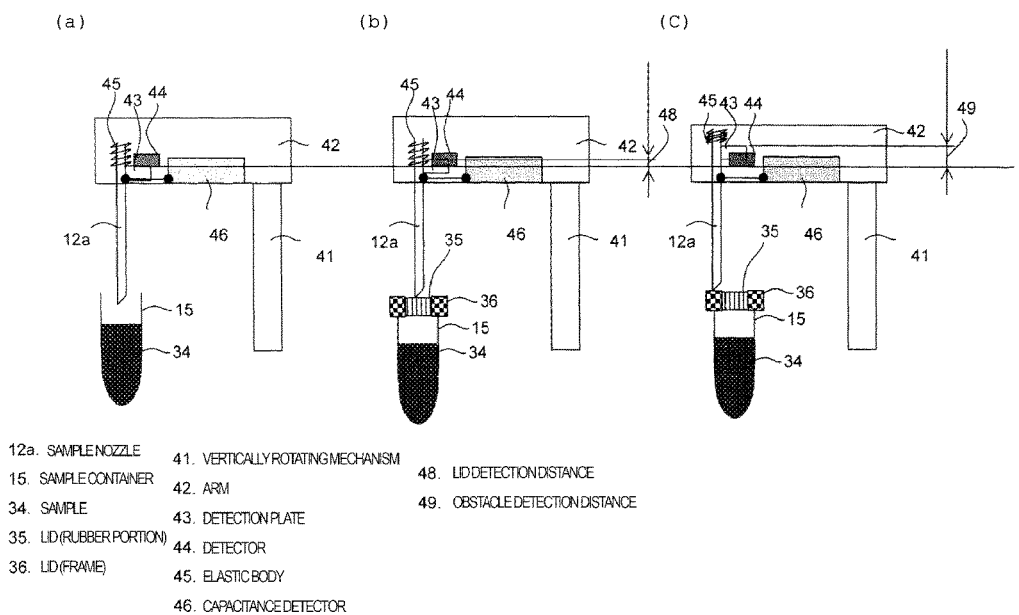
FIG. 4 is a view for describing a method of determining whether or not a lid of a sample container is present, based on a magnitude of external force applied to a sample nozzle, according to Embodiment 1 of the present invention.

FIG. 4 is a view for describing a method of determining whether or not the lid of the sample container is present and when the sample nozzle 12a comes into contact with the lid frame of the sample container or objects other than the lid, based on a magnitude of the external force applied to the sample nozzle 12a, according to Embodiment 1 of the present invention.

In FIGS. 3 and 4, the vertically rotating mechanism 41 causes the sample nozzle 12a to descend toward the sample container 15. In a case where the sample container 15 does not have the lid as illustrated in FIG. 4(a), based on a signal from the capacitance detector 46, the liquid level determination unit 21b determines that the sample nozzle 12a comes into contact with the liquid level of the sample 34 without the external force being applied to the sample nozzle 12a. Based on the determination, the operation commanding unit 21c supplies a descending operation stop signal to the vertically rotating mechanism 41. Then, the sample nozzle 12a moves to a predetermined position, and performs suction of the sample. The suction operation of the sample is performed by the controller 21 operating the sample pump 19.

As illustrated in FIG. 4(b), in a case where the sample container 15 has a rubber-made lid 35, if the sample nozzle 12a descends and hits the lid 35, the external force is applied to the sample nozzle 12a thereby the sample nozzle 12a is relatively moved inside the arm 42 as far as a lid detection distance 48, and the detector 44 detects the detection plate 43. Information that the detector 44 detects the detection plate 43 is transmitted to the obstacle determination unit 21a. Information that the sample nozzle 12a comes into contact with the lid 35 is stored into the operation commanding unit 21c together with the position information of the sample nozzle 12a.

If the sample nozzle 12a further continues to descend from a position illustrated in FIG. 4(b) and reaches the liquid level of the sample 34, the capacitance detector 46 and the liquid level determination unit 21b detect that the sample nozzle 12a reaches the sample 34. Subsequently, a command from the operation commanding unit 21c causes the vertically rotating mechanism 41 to stop the descending operation of the sample nozzle 12a, or after the sample nozzle 12a moves to the predetermined position, the suction operation of the sample 34 is performed by the sample pump 19.

As illustrated in FIG. 4(c), in a case where the sample container 15 has the lid 35 and the external force is applied after the sample nozzle 12a collides with the frame portion 36 of the lid 35, when the detection plate 43 is relatively moved inside the arm 42 as far as the lid detection distance 48, the detector 44 detects the detection plate 43. In this manner, the obstacle determination unit 21a determines that the sample nozzle 12a comes into contact with the lid 35 (rubber portion), and stores the information into the operation commanding unit 21c. Thereafter, the sample nozzle 12a continues to descend, thereby applying an excessive external force. When the detection plate 43 is relatively moved as far as an obstacle detection distance 49, the detector 44 and the obstacle determination unit 21a store information that the sample nozzle 12a comes into contact with the frame 36 of the lid or an obstacle other than the rubber portion of the lid, into the operation commanding unit 21c of the controller 21.

Then, the operation commanding unit 21c causes the vertically rotating mechanism 41 to cancel the subsequent descending and dispensing operation of the sample nozzle 12a. The operation commanding unit 21c causes the display unit 60 to display that an abnormal operation occurs (abnormal operation of the sample nozzle 12a), together with the sample number and the sample position in which the abnormal operation occurs.

As the detector 44, it is conceivable to use a sensor such as a photo interrupter.

In addition, in other words, the controller 21 causes the arm 42 to perform the descending operation in order for the sample nozzle to perform the dispensing operation of the sample. When a movement distance detected by the detector 44 is smaller than the lid detection distance or when the movement distance is equal to or greater than the lid detection distance and is smaller than the obstacle detection distance which is greater than the lid detection distance, the controller 21 commands the suction/discharge operation of the sample. When the movement distance detected by the detector 44 becomes the obstacle detection distance, the controller 21 causes the arm 42 to stop the descending operation, and causes the sample nozzle to stop the dispensing operation of the sample. Furthermore, when the movement distance detected by the detector 44 is smaller than the lid detection distance, the device can determine that the sample container 15 does not have the lid. When the movement distance is equal to or greater than the lid detection distance and is smaller than the obstacle detection distance which is greater than the lid detection distance, the device can determine that the sample container has the lid. Depending on whether or not the lid is present, the control of the dispensing operation may be changed.

As described above, the automatic analysis device has external force determination means (the external force detector 44, the obstacle determination unit 21a, the operation commanding unit 21c) which can determine the magnitude of the external force applied to the sample nozzle 12a through a plurality of stages (the lid detection distance 48 and the obstacle detection distance 49). Accordingly, it is possible to realize the automatic analysis device which can properly control the operation of the sample nozzle 12a and which can avoid damage to the sample nozzle 12a and the vertically rotating mechanism 41.

(Embodiment 2)

Next, Embodiment 2 according to the present invention will be described. According to Embodiment 2, an overall configuration of the automatic analysis device and a schematic configuration of the sample dispensing mechanism 12 are the same as those in the example illustrated in FIGS. 1 and 2. Thus, illustration and detailed description thereof will be omitted.

Figure 5:
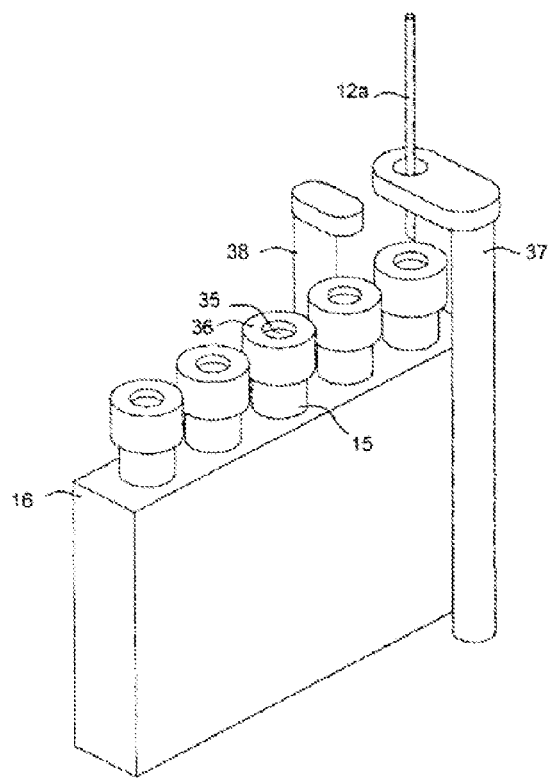
FIG. 5 is a view for describing a sample container fixing mechanism and a rack fixing mechanism, according to Embodiment 2 of the present invention.

FIG. 5 is a view for describing the sample container fixing mechanism 37 and the rack fixing mechanism 38 which utilize a contact target identification function of the sample nozzle 12a, according to Embodiment 2 of the present invention. The mechanisms 37 and 38 are a mechanism for avoiding the rack 16 and the sample container 15 from being raised in a case where the sample container 15 has the lid 35, when the sample nozzle 12a is separated from the sample container 15 after the sample nozzle 12a performs the suction of the sample.

Figure 6:
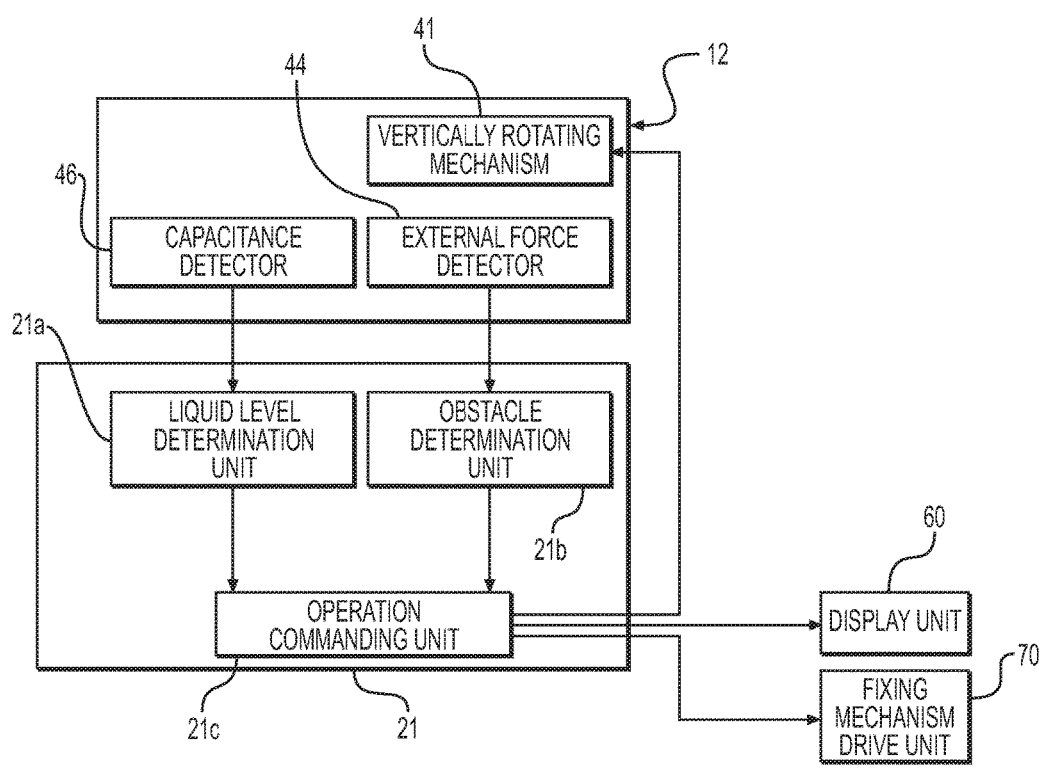
FIG. 6 is a functional block diagram relating to an operation control of a sample dispensing mechanism according to Embodiment 2 of the present invention.

FIG. 6 is a functional block diagram of the controller 21, which relates to an operation control of the sample dispensing mechanism 12 according to Embodiment 2 of the present invention. However, the block diagram illustrated in FIG. 6 is obtained by adding a fixing mechanism drive unit 70 for driving the sample container fixing mechanism 37 and the rack fixing mechanism 38 to the block diagram illustrated in FIG. 3. Other portions are the same as those in the block diagram illustrated in FIG. 3.

Figure 7:
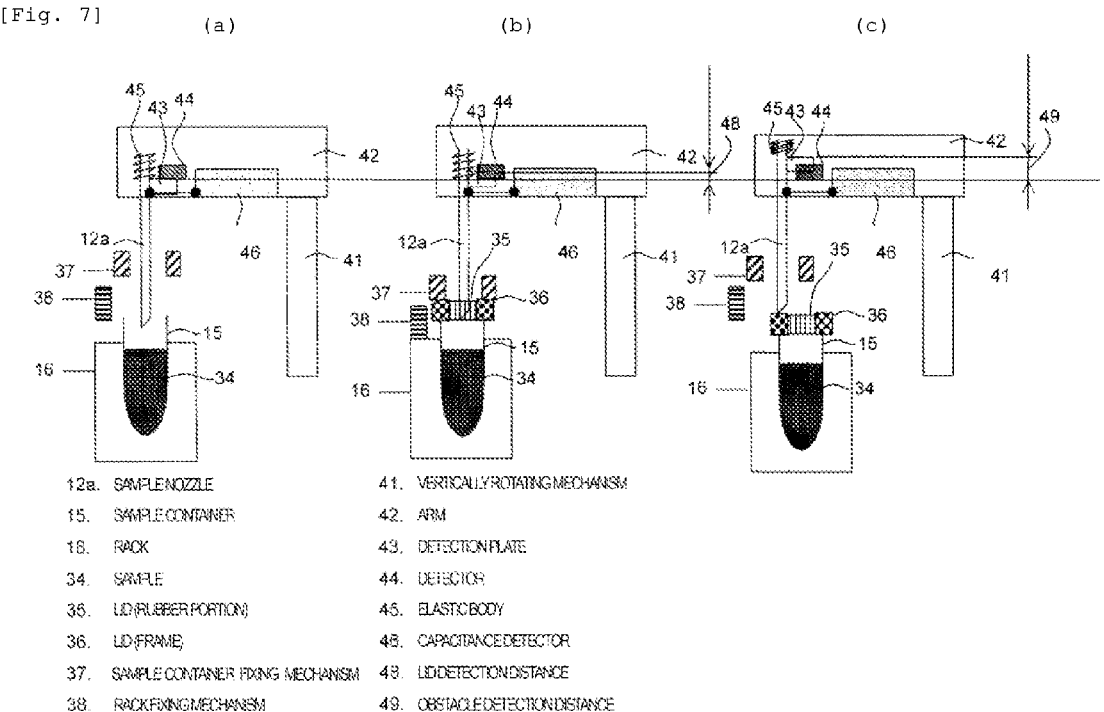
FIG. 7 is a view for describing a method of determining whether or not the lid of the sample container is present, based on the magnitude of the external force applied to the sample nozzle, according to Embodiment 2 of the present invention.

In addition, FIG. 7 is a view for describing a method of determining whether or not the lid of the sample container is present and when the sample nozzle 12a comes into contact with the lid frame of the sample container or objects other than the lid, based on a magnitude of the external force applied to the sample nozzle 12a, according to Embodiment 2 of the present invention. Embodiment 2 is the same as Embodiment 1 except that the sample container fixing mechanism 37 and the rack fixing mechanism 38 are added to Embodiment 1. Thus, other operations in Embodiment 2 are the same as those in Embodiment 1.

Figure 8:
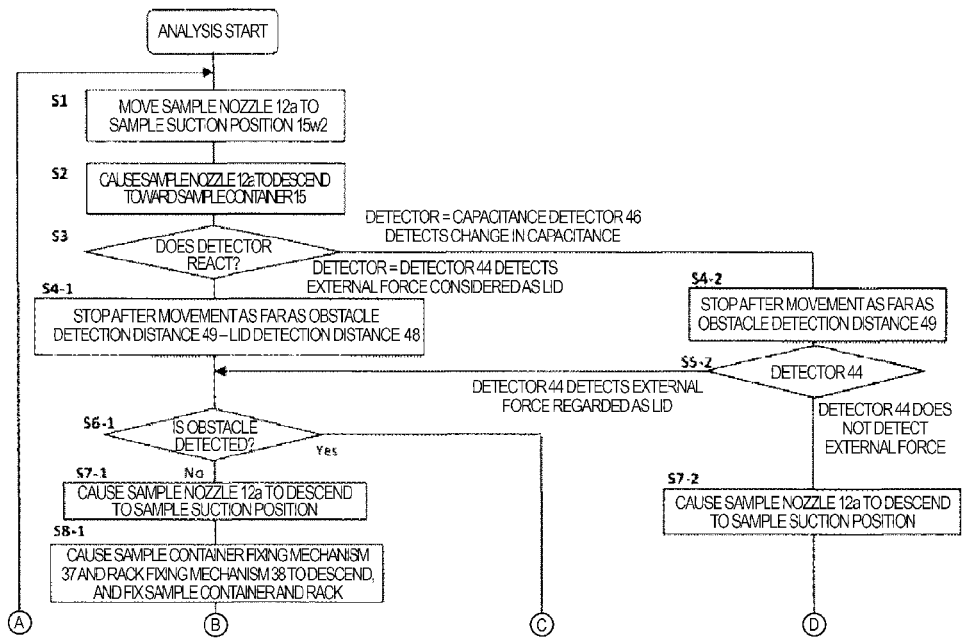
FIG. 8 is an operation flowchart according to Embodiment 2.
Figure 10:
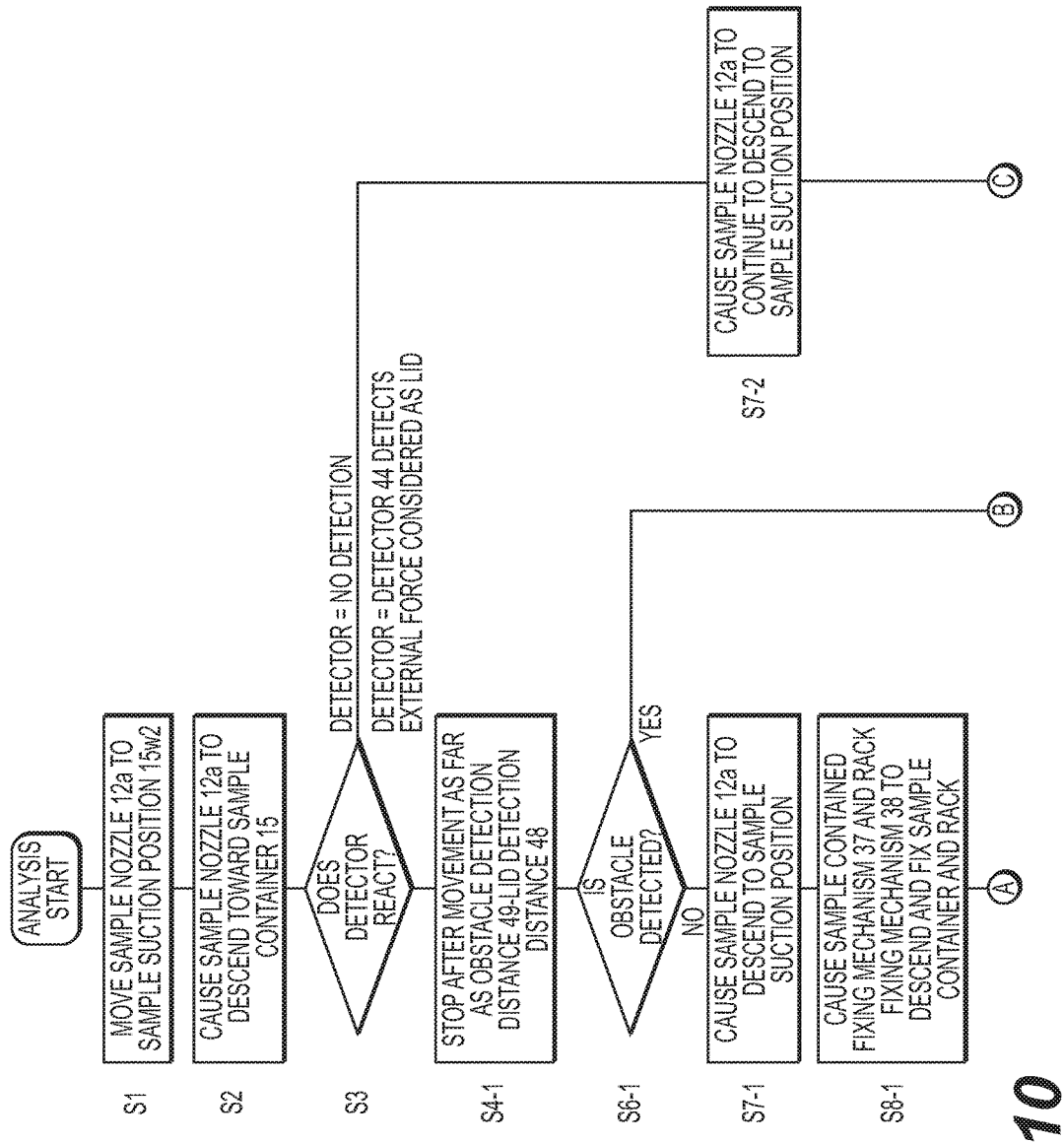
FIG. 10 is an operation flowchart according to Embodiment 2.
Figure 10:
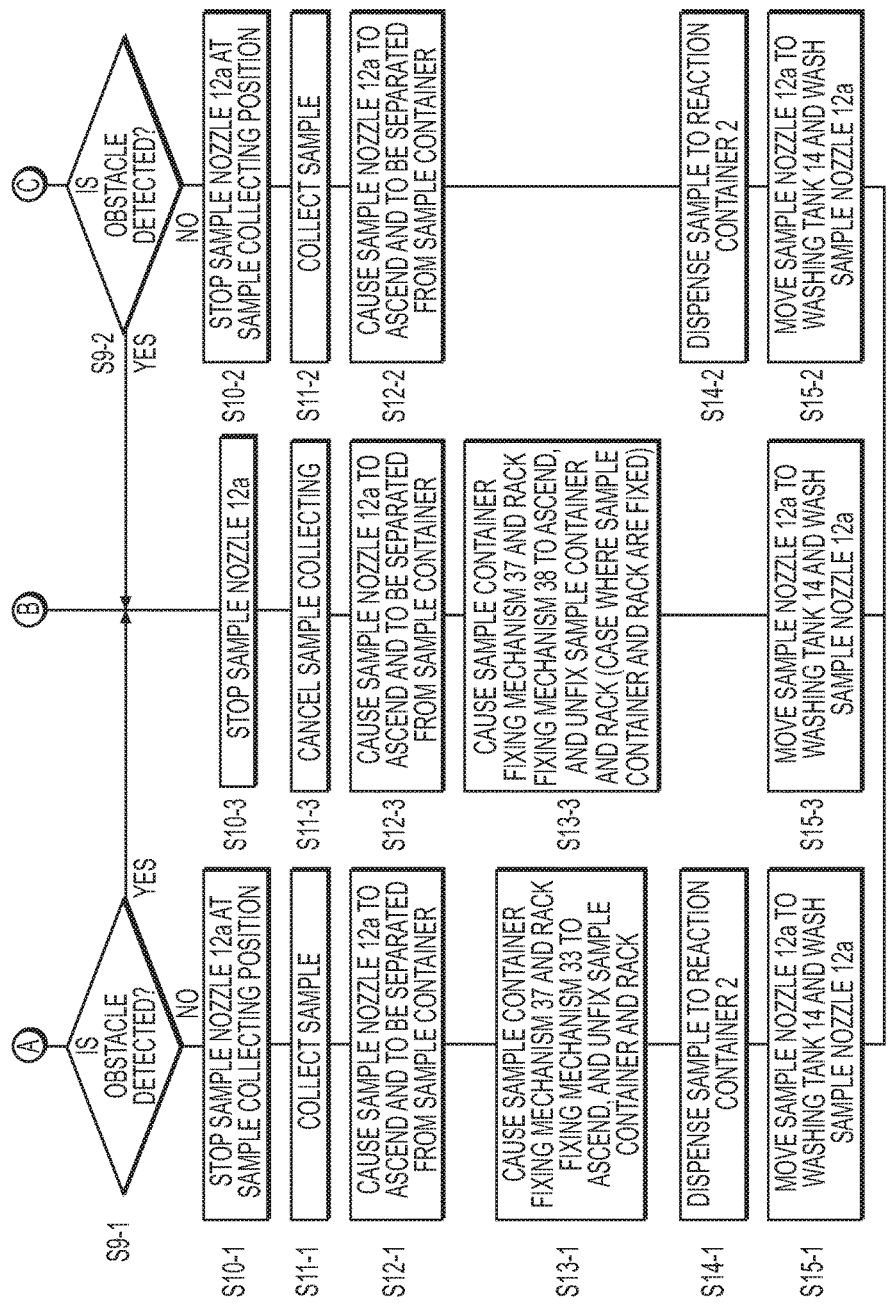

Furthermore, FIGS. 8 and 10 are operation flowcharts in Embodiment 2.

In FIG. 5, the sample container fixing mechanism 37 and the rack fixing mechanism 38 can be respectively and independently operated by the fixing mechanism drive unit 70. Similarly to Embodiment 1, if it is determined that the external force is applied to the sample nozzle 12a and the sample nozzle 12a comes into contact with the lid (rubber portion) 35 of the sample container 15, using this information as a trigger, the operation commanding unit 21c commands the fixing mechanism drive unit 70 to descend the sample container fixing mechanism 37 and the rack fixing mechanism 38 in order to respectively fix the sample container 15 and the rack 16.

The sample nozzle 12a is inserted into the sample container 15 so as to completely collect the sample, and is separated from the lid (rubber portion) 35. Thereafter, in accordance with a command from the operation commanding unit 21c, the fixing mechanism drive unit 70 causes the sample container fixing mechanism 37 and the rack fixing mechanism 38 to respectively ascend, and unfixes each sample container 15 and the rack 16 so as to retract to a position which does not obstruct the movement of the rack 16.

Next, referring to FIG. 7, an operation according to Embodiment 2 of the present invention will be described.

As illustrated in FIG. 7(a), in a case where the vertically rotating mechanism 41 causes the sample nozzle 12a to descend toward the sample container 15 and the sample container 15 does not have the lid, the external force is not applied to the sample nozzle 12a. In this case, in a state where the sample container fixing mechanism 37 and the rack fixing mechanism 38 are not operated, the sample nozzle 12a performs suction of the sample. This is because, when the sample container 15 has no lid, the sample nozzle 12a does not lift the rack 16 and the sample container 15 when the sample nozzle 12a is separated from the sample container 15. Accordingly, it is not necessary to fix the rack 16 and the sample container 15.

As illustrated in FIG. 7(b), in a case where the sample container 15 has the lid 35, if the sample nozzle 12a reaches the lid 35, the external force is applied to the sample nozzle 17a, thereby the detection plate 43 is relatively moved inside the arm 42 as far as the lid detection distance 48, and the detector 44 detects the detection plate 43. In this manner, the information that the sample nozzle 12a comes into contact with the lid (rubber portion) 35 is stored into the operation commanding unit 21c of the controller 21 together with the position information of the sample nozzle 12a. Using this information as a trigger, the sample container fixing mechanism 37 and the rack fixing mechanism 38 descend in order to respectively fix the sample container 15 and the rack 16.

Based on the position where the lid is detected by sample nozzle 12a which is stored inside the operation commanding unit 21c of the controller 21, the fixing mechanism drive unit 70 for driving the sample container fixing mechanism 37 can adjust a distance in which the sample container fixing mechanism 37 moves in order to fix the sample container 15.

In this manner, it is possible to control the mechanisms in accordance with the height of the lid which varies depending on a type of the sample container. It is also possible to prevent an excessive pressing load from being applied to a glass-made sample container and the like.

The sample container fixing mechanism 37 is provided in order to cause the sample container 15 to stay in the rack 16 by preventing the sample container 15 from being raised more than necessary when the sample nozzle 12a is separated from the sample container 15. Accordingly, based on the position where the lid is detected by the sample nozzle 12a which is stored inside the operation commanding unit 21c of the controller 21, the fixing mechanism drive unit 70 for driving the sample container fixing mechanism 37 can adjust a distance in which the sample container fixing mechanism 37 moves so as to stop several millimeters above the sample container 15. In this manner, without applying a load to a blood collection tube, when the sample nozzle 12a is separated from the sample container 15, the sample container 15 is prevented from being raised more than necessary. Accordingly, it is possible to achieve the purpose that the sample container 15 is caused to stay in the rack 16. The "fixing" described herein does not mean that the members are indispensably brought into contact with each other. Even when the sample container 15 is raised several millimeters, if the sample container 15 cannot be raised any further, this is included in the concept of the fixing.

Similarly, the rack fixing mechanism 38 is provided in order to cause the rack 16 to stay in the sample conveyance mechanism 17 by preventing the rack 16 from being raised more than necessary when the sample nozzle 12a is separated from the sample container 15. Accordingly, based on the information in which the lid is detected by the sample nozzle 12a which is stored inside the operation commanding unit 21c of the controller 21, the fixing mechanism drive unit 70 for driving the rack fixing mechanism 38 can adjust a distance in which the rack fixing mechanism 38 moves so as to stop several millimeters above the rack 16. That is, the "fixing" described herein does not mean that the members are indispensably brought into contact with each other. Even when the rack 16 is raised several millimeters, if the rack 16 cannot be raised any further, this is included in the concept of the fixing.

The sample nozzle 12a further continues to descend, and performs suction of the sample inside the sample container 15.

As illustrated in FIG. 7(c), in a case where the sample container 15 has the lid 35 and the external force is applied after the sample nozzle 12a collides with the frame portion 36 of the lid 35, thereby the detection plate 43 is relatively moved inside the arm 42 as far as the lid detection distance 48, and the detector 44 detects the detection plate 43. In this manner, it is determined that the sample nozzle 12a comes into contact with the lid 35 (rubber portion), and the information of the fact is stored into operation commanding unit 21c of the position controller 21 together with the position information of the sample nozzle 12a using this information as a trigger, the sample container fixing mechanism 37 and the rack fixing mechanism 38 descend in order to respectively fix the sample container 15 and the rack 16.

Thereafter, the sample nozzle 12a continues to descend, thereby applying an excessive external force and the detection plate 43 is relatively moved as far as the obstacle detection distance 49, then the detector 44 detects that the detection plate 43 is moved as far as the obstacle detection distance 49. In this manner, the information that the sample nozzle 12a comes into contact with the frame 36 of the lid or an obstacle other than the rubber portion 35 of the lid is stored into the operation commanding unit 21c of the controller 21. Using this information as a trigger, the sample container fixing mechanism 37 and the rack fixing mechanism 38 can cancel the descending for respectively fixing the sample container 15 and the rack 16.

In addition, the subsequent descending and dispensing operation of the sample nozzle 12a can also be cancelled.

FIGS. 8 and 10 are operation control flowcharts of a contact target determination function of the sample nozzle 12a and the sample container fixing mechanism 37 and the rack fixing mechanism 38 which utilize the contact target determination function, according to Embodiment 2 of the present invention. The operation control illustrated in FIG. 8 is performed by the controller 21. The control flow will be described in the order of Steps S1 to S15 in FIG. 8. The reference numeral j of Step Si-j indicates case classification of j=1, 2, and 3. In a case where J is 1, the sample container 15 has the lid. In a case where j is 2, the sample container 15 has no lid. Then, in a case where j is 3, the case indicates the control when it is determined that the sample nozzle 12a comes into contact with an obstacle other than the lid.

In FIG. 8, after Analysis Start, in Step S1, the sample nozzle 12a moves to the sample suction position 15w2. In Step S2, the sample nozzle 12a is caused to descend toward the sample container 15. In this stage, it is not identified whether or not the sample container 15 located at the sample suction position 15w2 has the lid.

Next, in Step S3, the detector 44 or 46 reacts. As described above, the detector includes the detector 44 which detects the external force applied to the nozzle 12a and the capacitance detector 46 which detects a capacitance change in the nozzle 12a.

In Step S3, in a stage where the detector 44 detects that the nozzle 12a is moved as far as the lid detection distance 48, it is not determined whether an object with which the nozzle 12a comes into contact is the lid (rubber portion) 35, or whether the object is an obstacle such as the lid (frame) 36. Accordingly, in Step S3, in a case where the detector 44 detects the external force, the process proceeds to Step S4-1, and in order to confirm whether or not the object with which the sample nozzle 12a comes into contact is the lid (rubber portion) 35, after the sample nozzle 12a is moved as far as a distance corresponding to "obstacle detection distance 49—lid detection distance 48", the sample nozzle 12a is stopped.

If the object with which the sample nozzle 12a comes into contact is not the lid (rubber portion) 35 and is the obstacle such as the lid (frame) 36, at a time point when the sample nozzle 12a moves as far as the above-described distance, as illustrated in FIG. 4(c), the detection plate 43 is relatively moved to a position of the obstacle detection distance 49 in the arm 42. Therefore, in the subsequent Step S6-1, a state of the detector 44 is confirmed. In this manner, it is possible to specify whether the contact target of the sample nozzle 12a is the lid 35 or the obstacle other than the lid 35.

In addition, the movement distance of the sample nozzle 12a is set to "obstacle detection distance 49—lid detection distance 48". In this manner, even if the contact target of the sample nozzle 12a is not the lid (rubber portion) 35 and is the obstacle such as the lid (frame) 36, a load applied to the sample nozzle 12a can be minimized. Therefore, it is possible to prevent damage to the mechanism.

In contrast, in Step S3, in a case where the capacitance detector 46 detects a capacitance change, it is not determined whether the sample nozzle 12a comes into contact with the liquid level of the sample of the sample container 15 having no lid, whether the capacitance is changed due to dew condensation water adhering to the lid (rubber portion) 35, or whether the sample nozzle 12a comes into contact with the lid (frame) 36 or other obstacles. Accordingly, the process proceeds from Step S3 to Step S4-2, and in order to confirm whether the object with which the sample nozzle 12a comes into contact is the liquid level of the sample, after the sample nozzle 12a moves as far as the distance corresponding to the "obstacle detection distance 49", the sample nozzle 12a is stopped.

If the object with which the sample nozzle 12a comes into contact is the liquid level of the sample of the sample container 15 having no lid, at a time point when the sample nozzle 12a moves as far as the distance corresponding to the above-described "obstacle detection distance 49", as illustrated in FIG. 4(a), the position of the sample nozzle 12a is not moved in the arm 42. In this case, in Step S5-2 where it is determined whether or not the subsequent detector 44 detects the external force, the detector 44 does not detect the external force applied to the sample nozzle 12a. Therefore, it is possible to identify that the sample container 15 has no lid.

In addition, if the object with which the sample nozzle 12a comes into contact is the lid (rubber portion) 35 or the obstacle such as the lid (frame) 36, while the sample nozzle 12a moves as far as the "obstacle detection distance 49", as illustrated in FIG. 4(b), the detection plate 43 is relatively moved to the position of the lid detection distance 48 in the arm 42. Accordingly, the detector 44 detects the external force applied to the sample nozzle 12a. In this manner, it is possible to recognize that the contact target is the lid (rubber portion) 35 or the obstacle such as the lid (frame) 36.

In addition, at a time point when the sample nozzle 12a moves as far as the "obstacle detection distance 49", in Step S6-1, a state of the detector 44 is confirmed as described above. In this case, it is possible to identify whether the contact target is the lid (rubber portion) 35 or the obstacle such as the lid (frame) 36, based on the external force applied to the nozzle 12a.

As described above, the sample nozzle 12a, the arm 42, and the controller 21 are provided with external force determination means having a simple configuration. Accordingly, based on a magnitude of the external force, it is possible to determine whether or not the sample container 15 has the lid, or whether the contact target of the sample nozzle 12a is the rubber of the lid, the frame of the lid, or the other obstacle which causes a possibility of damage to the nozzle if the nozzle descending operation is continued. Accordingly, it is possible to realize the sample dispensing mechanism which has the contact target identification function. Therefore, it is possible to prevent damage to the sample nozzle.

In Step S6-1, in a case where it is determined that the reagent container 15 is the container with specifications having the lid, the process proceeds to Step S7-1, the reagent nozzle 12a is caused to descend toward the sample suction position. The descending position may be a predetermined sample suction position, or the descending position of the nozzle 12a may be determined by detection means such as the capacitance detector 46 detecting the liquid level of the sample.

Next, in Step S8-1, the sample container fixing mechanism 37 and the rack fixing mechanism 38 are caused to descend so as to fix the sample container 15 and the rack 16.

The timing for fixing the sample container 15 and the rack 16 may be set before the sample nozzle 12a illustrated in Step S12-1 (to be described later) starts to be separated from the sample container 15.

If the fixing is continuously performed after the operation in which the sample nozzle 12a descends to the liquid level of the sample in Step S7-1, it is possible to shorten the operation required for the overall sample dispensing.

Before Step S7-1, the sample container 15 and the rack 16 can be fixed. In this case, it is possible to avoid a risk that the sample nozzle 12a may be buckled and damaged due to misalignment of the sample container 15 or the rack 16 which is caused by the external force applied when the sample nozzle 12a penetrates the lid (rubber) 35.

Subsequent to Step S8-1, in Step S9-1, it is determined whether or not the obstacle is detected by the descending of the sample nozzle 12a. In Step S9-1, in a case where the obstacle is not detected, the process proceeds to Step S10-1, and the sample nozzle 12a is stopped at a position for collecting the sample. Then, in Step S11-1, the sample is collected by the sample nozzle 12a.

In Step S10-1, if the sample container 15 and the rack 16 are fixed after the sample nozzle 12a is stopped at the position for collecting the sample, while the sample is collected in Step S11-1, or after the sample is collected, in Step S9-1 prior to Steps described above, the sample nozzle 12a is relatively moved in the arm 42 as far as the obstacle detection distance 49. In a case where the dispensing operation has to be cancelled, the sample container 15 and the rack 16 may not be unnecessarily fixed.

As an example of a case where the obstacle is detected in Step S9-1, a case is conceivable in which since the sample container is incorrectly installed or a non-standard sample container is installed, the sample nozzle 12a collides with the bottom of the container and an excessive external force is applied thereto.

Subsequent to Step S11-1, the process proceeds to Step S12-1, and the sample nozzle 12a is separated from the sample container 15. Thereafter, in Step S13-1, the sample container fixing mechanism 37 and the rack fixing mechanism 38 are caused to ascend so as to unfix the sample container 15 and the rack 16. Thereafter, in Step S14-1, the sample is dispensed to the reaction container 2 on the reaction disc 1. Then, in Step S15-1, the sample nozzle 12a is moved to the washing tank 14, and is washed so as to be provided for the subsequent dispensing.

As described above, the automatic analysis device has the external force determination means which can determine the magnitude of the external force applied to the sample nozzle 12a through a plurality of stages. Accordingly, even when the sample container 15 has the lid, the sample dispensing can be continuously performed while the sample nozzle 12a is prevented from being damaged due to the incorrect installation of the container or due to the installation of the non-standard container.

In Step S5-2, in a case where the detector 44 does not detect the external force, the process proceeds to Step S7-2, and the sample nozzle 12a is caused to descend to the sample suction position. Subsequently, in Step S9-2, it is determined whether or not the obstacle is detected by the descending of the sample nozzle 12a. In Step S9-2, in a case where the obstacle is not detected, the process proceeds to Step S10-2, and the sample nozzle 12a is stopped at the position for collecting the sample. Then, in Step S11-2, the sample is collected by the sample nozzle 12a.

Subsequent to Step S11-2, the process proceeds to Step S12-2, and the sample nozzle 12a is separated from the sample container 15. Thereafter, in Step S14-2, the sample is dispensed to the reaction container 2 on the reaction disc 1. Then, in Step S15-2, the sample nozzle 12a is moved to the washing tank 14, and is washed so as to be provided for the subsequent dispensing.

With regard to the obstacle detection in Step S9-2, it is previously recognized that the sample container 15 has no lid. Accordingly, in a case where the obstacle is detected, for example, if it is determined that the sample nozzle 12a hits the bottom of the container, the burden on the sample nozzle 12a can be reduced.

Steps S10-3 to S15-3 illustrate a flow for cancelling the subsequent dispensing operation in a case where the obstacle is detected in Steps S6-1, S9-1, and S9-2.

In Step S10-3, the operation of the sample nozzle 12a is stopped. In Step S11-3, the collection of the sample is cancelled. When the sample dispensing is continuously performed for the subsequent sample, the sample nozzle 12a is caused to ascend in Step S12-3, and is separated from the sample container 15. In a case where the sample container 15 and the rack 16 are fixed, in Step S13-3, the sample container fixing mechanism 37 and the rack fixing mechanism 38 are caused to ascend and retract.

Then, in Step S15-3, the sample nozzle 12a is moved to the washing tank, and the sample nozzle 12a is washed so as to be provided for the subsequent sample dispensing.

FIG. 10 illustrates an embodiment in which the capacitance detector 46 is not used as an option in the operation control flowchart of the contact target determination function of the sample nozzle 12a, the sample container fixing mechanism 37 and the rack fixing mechanism 38 which utilize the contact target determination function illustrated in FIG. 8.

Step S1 and Step S2 are the same as the processes in FIG. 8.

Next, in Step S3, the operation is changed depending on whether or not the detector 44 reacts. The subsequent Step when the detector 44 detects the external force considered as the lid is the same as the process in FIG. 8.

In contrast, in a case where the detector 44 does not detect the external force considered as the lid, the device causes the sample nozzle 12a to continue to descend in Step S7-2. When the obstacle is detected in Step S9-2, the process proceeds to Step S10-3 similarly to FIG. 8, and the sample nozzle 12a is stopped.

In a case where the obstacle is not detected in Step S9-2, the subsequent operation is performed similarly to FIG. 8, and the sample is collected.

As described above, even in a case where the capacitance detector 46 is not provided, the sample dispensing can be performed by providing the contact target determination function of the sample nozzle 12a. Whether or not the liquid level of the sample is present cannot be determined by using the capacitance detector 46. Accordingly, the suction position is fixed, or the liquid level of the sample is detected by using another means and the sample nozzle 12a is stopped at a predetermined suction position. With regard to whether or not the liquid level of the sample is present during the suction, whether the sample suction is normally performed can be determined based on a pressure change in a pressure sensor installed inside a flow path, for example.

Regardless of whether or not to use the capacitance detector 46, a case is also conceivable where only the sample container fixing mechanism 37 is driven in Steps S8-1, S13-1, and S13-3. In this case, it is desirable that when the detector 44 detects the lid detection distance, the controller 21 causes the fixing mechanism drive unit 70 to move the sample container fixing mechanism 37 so as to fix the sample container, and that after the arm ascends and the sample nozzle is separated from the sample container, the sample container fixing mechanism 37 is moved so as to unfix the sample container.

Regardless of whether or not to use the capacitance detector 46, a case is also conceivable where any one of the above-described mechanisms of the sample container fixing mechanism 37 and the rack fixing mechanism 38 is provided so that only one mechanism performs the control in Steps S8-1, S13-1, and S13-3. In this case, it is desirable that when the detector 44 detects the lid detection distance, the controller 21 causes the fixing mechanism drive unit 70 to move any one of the above-described mechanisms described above so as to fix the rack or the sample container which is a fixing target of any one of the above-described mechanisms, and that after the arm ascends and the sample nozzle is separated from the sample container, the fixing target fixed by any one of the above-described mechanisms described above is unfixed.

As described above, Embodiment 2 according to the present invention can also achieve an advantageous effect which is the same as that according to Embodiment 1. Furthermore, according to Embodiment 2 of the present invention, the sample container fixing mechanism 37 and the rack fixing mechanism 38 are provided. Accordingly, it is possible to avoid the sample nozzle 12a from raising the rack 16 and the sample container 15 when the sample nozzle 12a is separated from the sample container 15. Therefore, it is possible to avoid a change in the installation position of the sample container 15 and damage to the sample container 15.

(Embodiment 3)

Next, Embodiment 3 according to the present invention will be described. According to Embodiment 3, an overall configuration of the automatic analysis device and a schematic configuration of the sample dispensing mechanism 12 are the same as those in the example illustrated in FIGS. 1 and 2. Thus, illustration and detailed description thereof will be omitted.

Embodiment 3 according to the present invention is an example which enables the sample nozzle 12a to more accurately identify a contact target.

Figure 9:
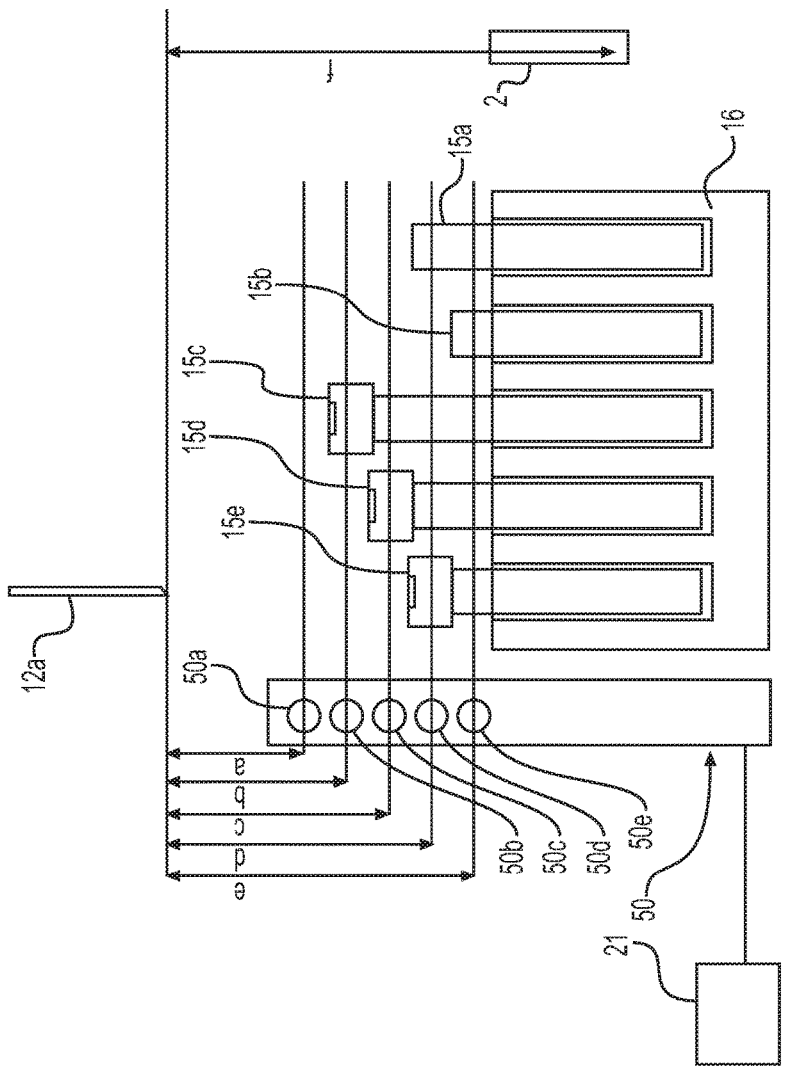
FIG. 9 is a view for describing a height sensor which is a main portion according to Embodiment 3 of the present invention.

FIG. 9 is a view for describing a height sensor 50 which is a main portion according to Embodiment 3 of the present invention. The height sensor 50 is arranged in the vicinity of the sample dispensing mechanism 12 and the rack 16, and detects the height of a plurality of the sample containers 15 accommodated in the rack 16.

In FIG. 9, the height sensor 50 is configured to include a beam sensor, for example, and has a plurality of sensors 50a, 50b, 50c, 50d, and 50e which are arrayed in series. Then, before the sample nozzle 12a has access to the sample container 15, the height sensor 50 detects which container having height dimensions a, b, c, d, and e of a certain degree is installed at each position of the rack 16, and the detection result is stored in the controller 21.

For example, in a case of a sample container 15e, a portion of the container is located on optical axes of the height sensors 50d and 50e. Accordingly, the sample nozzle 12a can recognize in advance that a contact target is not present up to the height c. Therefore, when the detector 44 and the capacitance detector 46 detect any contact before the sample nozzle 12a passes through the height c after performing the descending operation in order to collect the sample from the container 15e, it is immediately determined that the sample nozzle 12a comes into contact with the obstacle. In this case, the process does not proceed from Step S3 in FIG. 8 to Steps S4-1 and S4-2. The process proceeds from Step S3 to Step S10-3, and the descending operation of the sample nozzle 12a is immediately stopped.

In this manner, before the detection plate 43 is moved as far as the obstacle detection distance 49, in other words, before an extra load is applied to the sample nozzle 12a, it is possible to determine whether or not the object with which the sample nozzle 12a comes into contact is the obstacle other than the lid.

In addition, with regard to a place where an arrangement position is predetermined for an access target such as the reaction container 2, for example, a height f is registered in advance in the controller. In this case, when the detector 44 and the capacitance detector 46 detect any contact before the sample nozzle 12a passes through the height f after descending in order to discharge the sample to the reaction container 2, it is possible to immediately determine that the contact object is the obstacle.

As described above, it is possible to improve contact target identification accuracy of the sample nozzle 12a by providing the height sensors 50a to 50e and the contact target identification region setting function using height information at the access position of the sample nozzle 12a.

In addition, in a case where the sample nozzle 12a comes into contact with something outside the determination region for identifying the above-described contact target, without identifying the contact target, it is possible to determine that the sample nozzle 12a comes into contact with obstacle. Accordingly, it is not necessary to perform an extra operation such as an additional descending operation. Therefore, it is possible to reduce a load applied to the sample nozzle 12a.

FIG. 11 illustrates an example where the obstacle is not detected in Step S9-1 in the operation control flowchart of the contact target determination function of the sample nozzle 12a, the sample container fixing mechanism 37 and the rack fixing mechanism 38 which utilize the contact target determination function illustrated in FIG. 8.

Step S1 to Step S8-1 and Step S1 to Step S7-2 are the same as the processes in FIG. 8. The height sensor 50 illustrated in FIG. 9 can determine in advance that the sample container is incorrectly installed or that the non-standard sample container is installed. Accordingly, Step S9-1 can be omitted. When the detection of the obstacle is required in Step S9-1, the elastic body 45 for pressing the sample nozzle 12a against the arm 42 is needed to move as far as a restricted movement distance smaller than the obstacle detection distance 49 while the sample nozzle 12a penetrates the lid (rubber portion) 35 and moves to a predetermined suction position. Therefore, it is necessary to study whether to use the elastic body 45 which is relatively strong or whether to use a combination of a weak elastic body and a strong elastic body.

In contrast, in FIG. 11, an operation in Step S7-1 or the subsequent operation from S7-2 does not need to detect the obstacle. In other words, the elastic body 45 may move farther than the obstacle detection distance 49. Accordingly, it is possible to use the elastic body 45 which is relatively weak. A flow in Step S10-1 and the subsequent flow from Step S10-2 are the same as those in FIG. 8.

By lowering an elastic modulus of the elastic body 45, it is possible to reduce a load which is generated while the sample nozzle 12a comes into contact with the obstacle other than the lid (rubber portion) 35 and moves as far as the obstacle detection distance 49, and which is applied to the sample nozzle 12a by the elastic body 45.

The present embodiment adopts an example in which Step S9-1 can be omitted based on the flow in FIG. 8. However, Step S9-1 can be similarly omitted in an embodiment in which the capacitance detector 46 in FIG. 10 is not used as an option.

As described above, Embodiment 3 according to the present invention can also achieve an advantageous effect which is the same as that according to Embodiment 1. In addition, the automatic analysis device has the external force determination means (height sensor 50) which can determine the magnitude of the external force applied to the sample nozzle 12a through a plurality of stages. Accordingly, the operations including the related mechanisms in the dispensing operation can be optimized. The sample can be reliably dispensed while the contact target can be identified without causing damage to the sample nozzle 12a.

A configuration is adopted in which the external force applied to the above-described sample nozzle is determined by the detector 44 detecting the movement position of the detection plate 43. However, a pressure sensor may be arranged in a portion of the sample nozzle 12a inside the arm 42 so as to detect a pressure value actually applied to the sample nozzle 12a. In this manner, it is also possible to control the operation of the sample nozzle 12a and the vertically rotating mechanism 41.

In addition, according to the above-described example, both the sample container fixing mechanism 37 and the rack fixing mechanism 38 are caused to descend or are unfixed. However, in some cases, both mechanisms may not necessarily be provided, or even when both mechanisms are provided, both may not necessarily be driven. For example, in a case where the sample container fixing mechanism 37 is driven, each of "the sample container fixing mechanism 37 and the rack fixing mechanism 38" in each process in S9-1, S13-1, and S13-3 in FIGS. 8, 10, and 11 may be read as and replaced with "the sample container fixing mechanism 37". In addition, in a case where the rack fixing mechanism 38 is driven, similarly to the above-described case, each of "the sample container fixing mechanism 37 and the rack fixing mechanism 38" may be read as and replaced with "the rack fixing mechanism 38". If only any one of the mechanisms is driven since it is considered that the sample container is more likely to be raised than the rack, it is desirable to drive "the sample container fixing mechanism 37".

In addition, according to the above-described example, a case has been described where the present invention is applied to the sample dispensing operation of the reagent dispensing mechanism. However, the present invention is also applicable to a reagent dispensing operation of the reagent dispensing mechanism.

Furthermore, the suction operation of the sample has been mainly described as an example. However, the present invention is also applicable to a discharge operation of the sample or the reagent.

REFERENCE SIGNS LIST

1 REACTION DISC,
2 REACTION CONTAINER,
3 WASHING MECHANISM,
4 SPECTROPHOTOMETER,
5, 6 MIXING MECHANISM,
7, 8 REAGENT DISPENSING MECHANISM,
9 REAGENT DISC,
10 REAGENT BOTTLE,
11 SAMPLE DISPENSING MECHANISM,
11a SAMPLE NOZZLE,
12 SAMPLE DISPENSING MECHANISM,
12a SAMPLE NOZZLE,
13 WASHING TANK,
14 WASHING TANK,
15 SAMPLE CONTAINER,
15w SAMPLE SUCTION POSITION,
15w2 SAMPLE SUCTION POSITION,
16 RACK,
17 SAMPLE CONVEYANCE MECHANISM,
18 REAGENT PUMP,
19 SAMPLE PUMP,
20 WASHING PUMP,
21 CONTROLLER,
21a OBSTACLE DETERMINATION UNIT,
21b LIQUID LEVEL DETERMINATION UNIT,
21c OPERATION COMMANDING UNIT,
30 WASHING TANK,
31, 32, 33 WASHING TANK,
34 SAMPLE,
35 LID (RUBBER PORTION),
36 LID (FRAME),
37 SAMPLE CONTAINER FIXING MECHANISM,
38 RACK FIXING MECHANISM,
41 VERTICALLY ROTATING MECHANISM,
42 ARM,
43 DETECTION PLATE,
44 OBSTACLE (EXTERNAL FORCE) DETECTOR,
45 ELASTIC BODY,
46 CAPACITANCE DETECTOR,
48 LID DETECTION DISTANCE,
49 OBSTACLE DETECTION DISTANCE,
50 HEIGHT SENSOR,

60 DISPLAY UNIT,
70 FIXING MECHANISM DRIVE UNIT

The invention claimed is:

1. An automatic analysis device comprising:
a nozzle;
a dispensing mechanism that has an arm configured to move the nozzle in vertical and horizontal directions;
an elastic support member that is arranged in the arm, and that movably supports the nozzle in the vertical direction;
a relative movement distance detector that is arranged in the arm, and that is configured to detect a relative movement distance of the nozzle with respect to the arm;
a pump that is connected to the nozzle and configured to suction a liquid, which is a reagent or a sample, from a first container and to discharge the liquid into a second container;
a liquid level detector that is arranged in the arm unit, and that is configured to detect when the tip portion of the nozzle comes into contact with a liquid level,
a photometer configured to emit light inside the second container and detect light intensity of light from inside the second container; and
a controller configured to operate the dispensing mechanism, the pump, and the photometer, and to analyze the sample inside the second container based on the light intensity detected by the photometer,
wherein the controller is further configured to:
operate the arm to lower the nozzle in the vertical direction toward the first container,
determine, when the relative movement distance of the nozzle toward the first container with respect to the arm which is detected by the relative movement distance detector reaches a predetermined first detection distance, that the tip portion of the nozzle comes into contact with a lid portion of the first container into which the nozzle can be inserted,
determine, when the relative movement distance of the nozzle toward the first container with respect to the arm which is detected by the relative movement distance detector reaches a predetermined second detection distance larger than the first detection distance, that the tip portion of the nozzle comes into contact with a member into which the nozzle cannot be inserted,
when the relative movement distance of the nozzle toward the first container is less than the second detection distance and when the liquid level detector detects the liquid level in the first container, operate the pump to suction the liquid from the first container, and
when the relative movement distance of the nozzle toward the first container reaches the second detection distance, stop the arm from lowering the nozzle toward the first container.

2. The automatic analysis device according to claim 1,
wherein the controller is further configured to:
operate the arm to lower the nozzle in the vertical direction toward the second reaction container,
determine, when the relative movement distance of the nozzle toward the second container with respect to the arm which is detected by the relative movement distance detector reaches the second detection distance, that the tip portion of the nozzle comes into contact with a member into which the nozzle cannot be inserted, and
when the relative movement distance of the nozzle toward the second container reaches the second detection distance, stop the arm from lowering the nozzle toward the second container, and
wherein the controller is further configured to:
when the relative movement distance of the nozzle toward the first container reaches the second detection distance, stop the arm from lowering the nozzle toward the first container.

3. The automatic analysis device according to claim 2, further comprising:
a rack that linearly arranges and accommodates a plurality of sample containers including the first container;
a movable rack fixing mechanism that fixes the rack; and
wherein the controller is further configured to:
cause, when the relative movement distance of the nozzle toward the first container with respect to the arm which is detected by the relative movement distance detector reaches the first detection distance, the rack fixing mechanism to move so as to fix the rack, and
cause, when the arm is operated to raise and separate the nozzle from the first container, the rack fixing mechanism to move the rack fixing mechanism to unfix the rack.

4. The automatic analysis device according to claim 1, further comprising:
a display unit,
wherein the controller is further configured to:
display, when the relative movement distance of the nozzle toward the first container is greater than or equal to the second detection distance, an abnormality notification including an identification number and a location of the first container on the display unit, and
display, when the relative movement distance of the nozzle toward the second container is greater than or equal to the second detection distance, an abnormality notification including an identification number and a location of the second container on the display unit.

5. The automatic analysis device according to claim 1,
wherein the relative movement distance detector has an obstacle detection plate which is fixed to the nozzle, and an obstacle detector fixed to the arm which detects the relative movement distance of the detection plate fixed to the nozzle.

6. The automatic analysis device according to claim 1, further comprising:
a rack that linearly arranges and accommodates a plurality of sample containers including the first container;
a movable rack fixing mechanism that fixes the rack;
a movable sample container fixing mechanism that fixes the first container accommodated in the rack; and
wherein the controller is further configured to:
cause, when the relative movement distance of the nozzle toward the first container with respect to the arm which is detected by the relative movement distance detector reaches the first detection distance, the rack fixing mechanism and the sample container fixing mechanism to move so as to fix the rack and the first container, and
cause, when the arm is operated to raise and separate the nozzle from the first container, the fixing mechanism drive unit to move the rack fixing mechanism and the sample container fixing mechanism so as to unfix the rack and the first container.

7. The automatic analysis device according to claim 1, further comprising:
a rack that linearly arranges and accommodates a plurality of sample containers including the first container; and a height detection sensor that detects a height dimension of the first container accommodated in the rack, wherein the controller is further configured to determine, when the relative movement distance of the nozzle toward the first container reaches the first detection distance and before the nozzle reaches the detected height dimension of the first container, that the nozzle comes into contact with an obstacle while the nozzle is lowered toward the first container.

8. An automatic analysis device comprising:

a nozzle;

a dispensing mechanism that has an arm configured to move the nozzle in vertical and horizontal directions;

an elastic support member that is arranged in the arm, and that movably supports the nozzle in the vertical direction;

a relative movement distance detector that is arranged in the arm, and that is configured to detect a relative movement distance of the nozzle with respect to the arm;

a pump connected to the nozzle and configured to suction a liquid, which is a reagent or a sample, from a first container and to discharge the liquid into a second container;

a photometer configured to emit light inside the second container and detect light intensity of light from inside the second container; and a controller configured to operate the dispensing mechanism, the pump, and the photometer, and to analyze the sample inside the second container based on the light intensity detected by the photometer, wherein the controller is further configured to:

operate the arm to lower the nozzle in the vertical direction toward the first container, determine, when the relative movement distance of the nozzle toward the first container with respect to the arm which is detected by the relative movement distance detector reaches a predetermined first detection distance, that the tip portion of the nozzle comes into contact with a lid portion of the first container into which the nozzle can be inserted, determine, when the relative movement distance of the nozzle toward the first container with respect to the arm which is detected by the relative movement distance detector reaches a predetermined second detection distance larger than the first detection distance, that the tip portion of the nozzle comes into contact with a member into which the nozzle cannot be inserted, when the relative movement distance of the nozzle toward the first container is less than the first detection distance at a predetermined suction position, operate the pump to suction the liquid from the first container, when the relative movement distance of the nozzle toward the first container is less than the second detection distance at the predetermined suction position, operate the pump to suction the liquid from the first container, when the relative movement distance of the nozzle toward the first container reaches the second detection distance, stop the arm from lowering the nozzle toward the first container.

9. The automatic analysis device according to claim 8, further comprising:

a rack that linearly arranges and accommodates a plurality of sample containers including the first container;

a movable sample container fixing mechanism that fixes the first container accommodated in the rack; and wherein the controller is further configured to:

cause, when the relative movement distance of the nozzle toward the first container with respect to the arm which is detected by the relative movement distance detector reaches the first detection distance, the sample container fixing mechanism to move so as to fix the first container, and cause, when the arm is operated to raise and separate the nozzle from the first container, the sample container fixing mechanism to move so as to unfix the first container.

* * * * *